United States Patent [19]

Dougherty et al.

[11] Patent Number: 5,329,036

[45] Date of Patent: Jul. 12, 1994

[54] (ALPHA, OMEGA)PHENYLETHYNYL SILOXANE MONOMERS, OLIGOMERS, AND POLYMERS THEREOF

[75] Inventors: Thomas K. Dougherty, Playa Del Rey; William E. Elias, El Segundo, both of Calif.

[73] Assignee: Hughes Aircraft Company, Los Angeles, Calif.

[21] Appl. No.: 939,326

[22] Filed: Sep. 2, 1992

[51] Int. Cl.$^5$ ............................................. C08F 7/08
[52] U.S. Cl. ..................................... 556/453; 528/32
[58] Field of Search ........................... 556/453; 528/32

[56] References Cited

U.S. PATENT DOCUMENTS 3,096,303  7/1963  Caprino ............................... 556/453
5,055,593  10/1991  Sasaki et al. ........................ 549/214

FOREIGN PATENT DOCUMENTS 1165869  3/1964  Fed. Rep. of Germany .
307092  8/1991  U.S.S.R. .

OTHER PUBLICATIONS

Mantecon et al "Diethynyl terminated siloxane bases" (bisazomethine schiff base), *Polymer Bulletin*, vol. 23, 1990, pp. 439–445.

Maud gal et al "Siloxane containing addition polyimides. II. Acetylene–Terminated polyimides, " *Chemical Abstracts*, vol. 105, No. 16, Oct. 20, 1986, abstract No. 135021q.

Y. Nagase et al, "Chemical Modification of Poly(substitued–acetylene). I. Syntheis and Gas Permeability of Poly(1–trimethylsilyl–1–propyne)/Poly(dimethylsiloxane) Graft Copolymer", in *Journal of Polymer Science, Part B: Polymer Physics*, vol. 29, pp. 171–179 (1991).

*Primary Examiner*—Ralph H. Dean
*Attorney, Agent, or Firm*—M. E. Lachman; M. W. Sales; W. K. Denson-Low

[57] ABSTRACT

Novel acetylene-terminated silicone monomers with (a) silane (Si—H) functionalities, (b) silanol (Si—OH) functionalities, or (c) (alpha,omega)phenylethynyl terminated siloxanes, and a novel synthetic route. The (alpha,omega)phenylethynyl-terminated siloxane monomers are prepared, starting with 1,3-bromobenzene, which is converted to 3-TMS-ethynylbromobenzene, where TMS represents the trimethylsilyl group, by reacting 1,3-dibromobenzene with trimethylsilylacetylene and triethylamine in the presence of a palladium catalyst. The 3-bromo-TMS protected phenyl acetylene is then reacted with an alkyllithium compound, such as n-butyllithium, or with magnesium to form the corresponding lithio or Grignard compound, respectively, followed by reaction with a halogenated compound, such as chlorodimethylsilane, to form 3-trimethylsilylethynylphenyldimethyl silane. Next, the TMS protected ethynylphenyl silane is subjected to deprotection and methanolysis of the Si—H bond to form 3-ethynylphenyldimethyl methoxy silane, employing methanol. This silane is then hydrolyzed to form the corresponding silanol. Finally, the silanol is then condensed by known methods to form the disiloxane. The disiloxane monomer can be reacted with a cyclic siloxane, having $\geq 3$ silicon atoms, each independently substituted with hydrogen, $C_1$ to $C_6$ alkyl, phenyl, or phenyl substituted with one or more alkyl or halogen groups, to form oligomers. Both monomers and oligomers form thermoset polymers by heating to a temperature of at least about 250° C.

4 Claims, No Drawings

(ALPHA, OMEGA)PHENYLETHYNYL SILOXANE MONOMERS, OLIGOMERS, AND POLYMERS THEREOF

BACKGROUND OF THE INVENTION

1. Field of the Invention

The present invention relates generally to silicon-containing compounds, methods for the preparation of such compounds, and polymers thereof. More particularly, the present invention relates to phenylacetylene terminated siloxane monomers and higher oligomers, which can be polymerized to give thermoset resins, rubbers, and glasses.

2. Description of Related Art

Thermoset silicone resins are known to have a limited shelf life once formulated. They may cure only after the addition of a catalyst or curing agent. They may only cure in the presence of moisture or in low cross-section. Finally, they do not give the desired thermal stability or range of thermomechanical properties. Although a variety of different curing silicone resins are available, none offers the advantages of an acetylene cured system as described herein.

Acetylene-terminated imides and oligomers and polymers thereof are known; these are available from National Starch and Chemical Company under the tradename THERMID. They are useful for composite and electronic manufacture. It is desirable to extend this technology and to provide toughness to these polymers.

There remains a need for a class of thermoset monomers and polymers that have improved thermal stability and thermomechanical properties.

SUMMARY OF THE INVENTION

In accordance with the invention, (alpha,omega) phenylethynyl siloxane monomers and oligomers and polymers thereof are provided. An example of the monomer is bis(3-ethynylphenyl)tetramethyldisiloxane, where in place of the methyl groups may be any of the lower alkyl, phenyl, or substituted phenyl groups.

The exemplary monomer is made by replacing one of the bromines on 1,3-dibromobenzene with a substituted acetylene, such as TMS-acetylene, where TMS represents the trimethylsilyl group. Thus, 1,3-dibromobenzene is converted to 3-TMS-ethynylbromobenzene by reacting 1,3-dibromobenzene with trimethysilylacetylene and triethylamine in the presence of a palladium catalyst. The 3-bromo protected phenyl acetylene is then reacted with an alkyllithium compound, such as n-butyllithium, or with magnesium to form the corresponding lithio or Grignard compound, respectively, followed by reaction with a halogenated compound, such as chlorodimethylsilane, to form 3-trimethylsilylethynylphenyldimethyl silane. Next, the protected ethynylphenyl silane is subjected to deprotection and methanolysis of the Si—H bond to form 3-ethynylphenyldimethyl methoxy silane, employing methanol. This silane is then hydrolyzed to form the corresponding silanol. Finally, the silanol is then condensed by known methods to form the disiloxane.

The disiloxane monomer can be reacted with a cyclic siloxane, having ≧3 silicon atoms, each independently substituted with hydrogen, $C_1$ to $C_6$ alkyl, phenyl, or phenyl substituted with one or more alkyl or halogen groups, to form oligomers. Both monomers and oligomers form thermoset polymers by heating to a temperature of at least about 250° C.

The monomers, oligomers, and polymers formed from the monomers and oligomers offer several advantages. The monomers and oligomers are high boiling mobile liquids and as such are useful in the production of composites, coatings, and other resin systems. Because of the nature of the high temperature thermoset acetylene part, the cured monomers and oligomers are produced with little shrinkage during cure. Also, the crosslink site is a very thermally stable acetylene cured site and this crosslink imparts improved thermal stability to the cured polymers. Because of the nature of the siloxane oligomer, the materials made are tailorable as to glass transition temperature, coefficient of thermal expansion, and processibility. In addition, the siloxane site offers resistance to heat and, importantly, to atomic oxygen degradation (as experienced in earth orbit).

Further, copolymers of the monomers or oligomers of the invention may be formed with acetylene-terminated imide resins. The monomers and oligomers serve to toughen the copolymers.

DESCRIPTION OF THE PREFERRED EMBODIMENTS

The following synthetic particulars and polymerization procedures describe in detail this invention. In addition, properties of the resulting cured materials are also described. The (alpha,omega)phenylethynyl siloxane monomer is represented as Formula A:

Formula A where $R^1$, $R^2$, $R^3$, and $R^4$ are each selected from the group consisting of $C_1$ to $C_6$ alkyl, phenyl, or phenyl substituted with one or more $C_1$ to $C_6$ alkyl or halogen groups. The synthesis of this monomer is shown below and described thereafter:

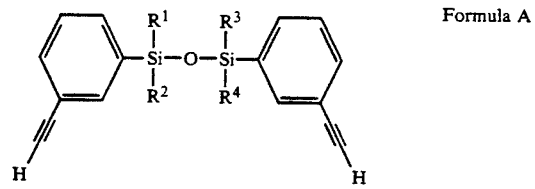

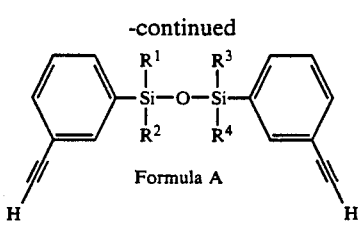

Formula A

As depicted in the reaction sequence above, 1,3-dibromobenzene is converted to a protected 3-ethynylbromobenzene (1). This is accomplished by reacting 1,3-dibromobenzene with a substituted acetylene, $R^5$—C≡C—H. $R^5$ may be a functional group that leaves easily in a subsequent reaction, leaving H in its place; an example is the trimethylsilyl (TMS) group. Other examples of $R^5$ leaving groups include the acetals, ketones, ketals, hydroxymethyl, tetrahydropyran-protected hydroxymethyl, dimethylcarbinol, ethyl vinyl ether protected carbinol, and ethyl ester. The removal of these groups often requires several steps and/or strongly alkaline media.

Alternatively, $R^5$ may be a functional group which remains, thereby affording tailorability of the properties of the final monomer, oligomer, or polymer; examples include phenyl, substituted phenyl, and $C_1$ to $C_6$ alkyl.

It will be appreciated that the protected 3-ethynylbromobenzene (1) can be used to make a number of substituted phenylacetylenes other than silated phenylacetylenes.

The 3-bromo protected phenyl acetylene (1) is then reacted with an alkyllithium compound, such as n-butyllithium, or with magnesium to form the corresponding lithio or Grignard compound, respectively, followed by reaction with a halogenated compound, such as chlorodimethylsilane, to form the corresponding silane compound (2). Compound (2) is useful for the covalent attachment of phenylacetylene to vinyl-containing molecules or polymers.

Next, the protected ethynylphenyl silane (2) is subjected to deprotection and alcoholysis of the Si—H bond to form 3-ethynylphenyldi(substituted) alkoxy silane (3), employing an alkyl or aryl alcohol, $R^6$—OH such as methanol, where $R^6$ is selected from the group consisting of $C_1$ to $C_6$ alkyl, phenyl, or phenyl substituted with one or more $C_1$ to $C_6$ alkyl or halogen groups. The latter siloxycompound (3) is useful for covalently attaching the phenyl acetylene linkage to a silicate or other metal alkoxide linkage in a "sol-gel" reaction. The resulting acetylene-containing sol, gel, or glass may serve as an anchor for further polymerization of acetylene or phenylacetylene. Properly doped (oxidized or reduced) polyacetylene and polyphenylacetylene are well-known electrically conductive polymers. Hence, compounds such as siloxy (3) may be useful for chemical stabilization and covalent attachment of the polymers (poly(phenyl)acetylenes) to sols, gels, and glasses. This could be accomplished by attaching the anchor and subsequently performing an acetylene polymerization reaction on the attached materials.

Additionally, optically active diacetylene molecules are known. Oxidative addition of other acetylene molecules to the covalently anchored acetylene could give covalently attached diacetylenes to the sol, gel, or glass.

The siloxy compound (3) is then hydrolyzed to form the corresponding silanol (4). The latter compound is useful for the same purposes as the siloxy compound (3), as described above.

The silanol (4) is then condensed by known methods, described, for example, in U.S. Pat. No. 5,075,475, to form bis(3-ethynylphenyl)tetra(alkyl or aryl)-disiloxane (Formula A).

The siloxane monomer (Formula A) can be reacted with a cyclic siloxane having ≧3 silicon atoms, each substituted with $R^7$ and $R^8$, to form oligomers having Formula B, as shown below. A catalyst such as tetramethyl ammonium hydroxide ($NMe_4OH$) may be used.

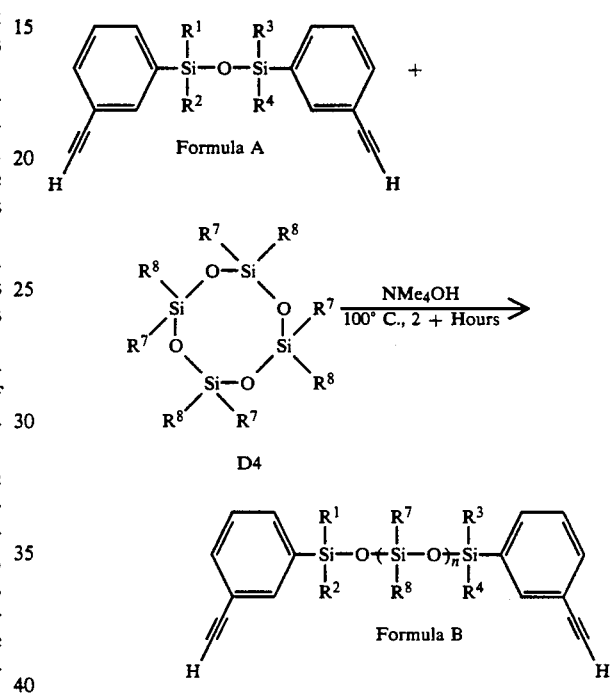

where $R^7$ and $R^8$ are each selected from the group consisting of hydrogen, $C_1$ to $C_6$ alkyl, phenyl, or phenyl substituted with one or more $C_1$ to $C_6$ alkyl or halogen groups and n=1 to 20. A preferred example of the cyclic siloxane is octamethyl tetracyclosiloxane.

It will be appreciated that where n=0, the compound is that of Formula A. Accordingly, for convenience, Formula B will be used hereinafter to represent both the monomer (n=0) and oligomers (n=1 to 20).

The monomers and oligomers thereof can be used to chemically stabilize polyacetylenes and diacetylenes into siloxane rubbers. The attachment would not be covalent, but would rely on the monomers or oligomers as a chemical compatibilizer.

The reaction sequence for the preferred embodiment is depicted below, where Me is the methyl group:

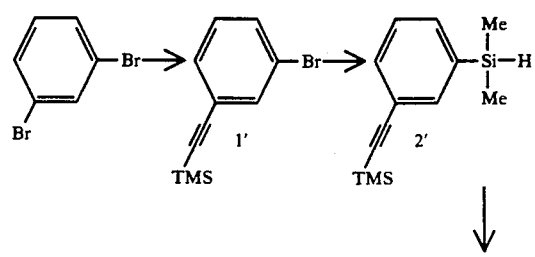

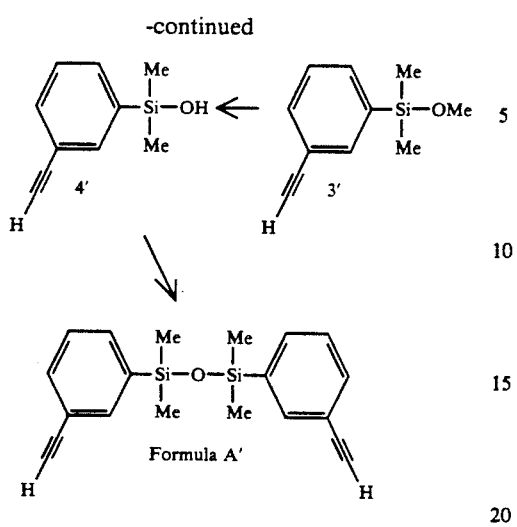

Formula A'

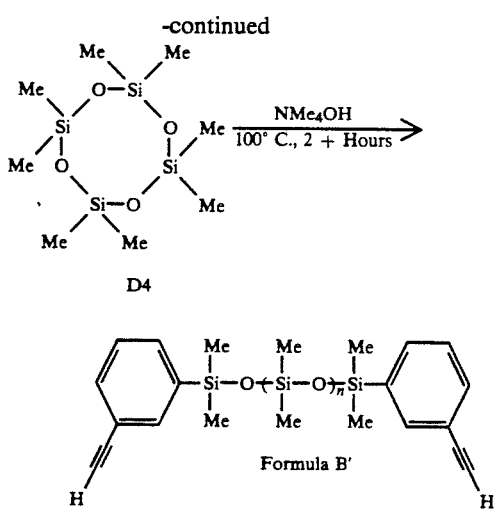

D4

Formula B'

In the preferred embodiment, 1,3-dibromobenzene is converted to 3-TMS-ethynylbromobenzene (1'), where TMS represents the trimethylsilyl group. This is accomplished by reacting 1,3-dibromobenzene with trimethysilylacetylene and triethylamine in the presence of a palladium catalyst.

The 3-bromo-TMS protected phenyl acetylene (1') is then reacted with an alkyllithium compound, such as n-butyllithium, or with magnesium to form the corresponding lithio or Grignard compound, respectively, followed by reaction with a halogenated compound, such as chlorodimethylsilane, to form 3-trimethylsilylethynylphenyldimethyl silane (2').

Next, the TMS protected ethynylphenyl silane (2') is subjected to deprotection and methanolysis of the Si—H bond to form 3-ethynylphenyldimethyl methoxy silane (3'), employing methanol. This silane is then hydrolyzed to form the corresponding silanol (4').

The silanol is then condensed by known methods, described, for example, in U.S. Pat. No. 5,075,475, to form bis(3-ethynylphenyl)tetramethyldisiloxane (Formula A').

The siloxane monomer (Formula A') can be reacted with a cyclic siloxane, having $\geq 3$ silicon atoms, each substituted with $R^7$ and $R^8$, to form oligomers having Formula B', as shown below. The preferred cyclic siloxane is octamethyl tetracyclosiloxane (D4).

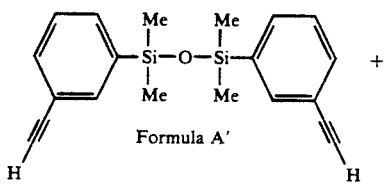

Formula A'

Specifically, 1,3-bis(3-ethynylphenyl)tetramethyldisiloxane (Formula B') is reacted with octamethyl tetracyclosiloxane (D4) in the presence of base, such as tetramethylammonium hydroxide, to form the oligomers. A mixture of oligomers is obtained.

In the oligomer mixture, the average value of n is dependent on the ratio of the disiloxane (Formula A) and the cyclic siloxane (D4) at the start of the reaction. The greater the amount of D4, the higher the average value of n.

Both the monomer and oligomers are polymerizable, and form thermoset polymers by heating to a temperature of at least about 250° C. Crosslinkages occur between acetylene functionalities.

Also, it is well-known that silicones are good materials for use as gas separation membranes, especially since they have excellent oxygen permeability. The polymers of Formula A and of Formula B and all of their copolymers may have useful and interesting properties in the nature of gas permeability and separation. These polymers and copolymers are also useful as adhesives and for forming composites.

Copolymers which incorporate the monomers or oligomers of the invention in acetylene-terminated imides are formed by dissolving the monomer or oligomer and the imide in a suitable solvent to form clear, homogeneous solutions. Examples of suitable solvents include tetrahydrofuran, methyl isobutyl ketone, dimethyl acetamide, and cyclohexanone. Other common solvents have not been found to dissolve both the silicone and the imide to form such solutions. The solutions are conveniently cast onto a substrate and cured at an elevated temperature to form the copolymer. The curing temperature can go as high as about 300° C. A ramping cure cycle may be employed, utilizing a plurality of intermediate temperatures, and holding at each temperature for a period of time. The acetylene polymerization in the silicone rubbery phase acts to chemically adhere to and compatibilize the phenylacetylene to the polyimide phase.

Examples of acetylene-terminated polyimides useful in the practice of the invention are shown below.

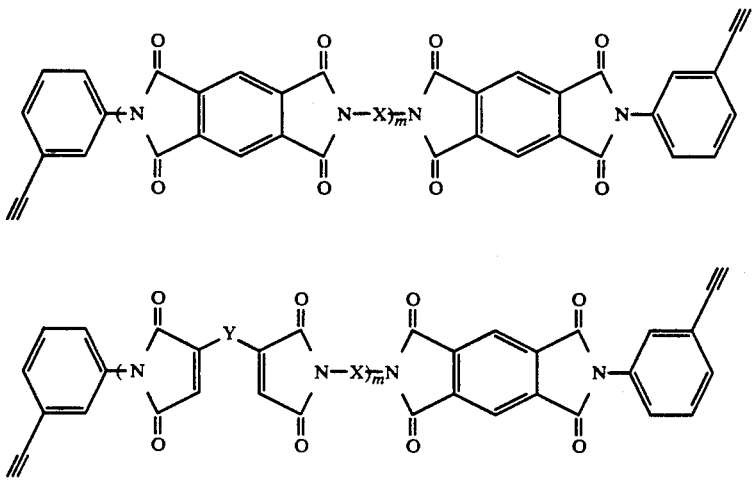

where X and Y are independently either a direct bond or a divalent radical selected from the group consisting of —CH$_2$—, —C(CH$_3$)$_2$—, —C(CF$_3$)$_2$—, —O—, —S—, —CO—, —SO$_2$—, and —Si(CH$_3$)$_2$— and m has a value ranging from 0 to 20. Where m=0, the compound is considered to be an imide; where m=1 to 20, the compounds are considered to be polyimides. However, for the purposes of this invention, all such compounds are termed "imides" herein. Specific acetylene-terminated imides are commercially available under the trademark THERMID from National Starch and Chemical Company, Bridgewater, N.J. The copolymers of the present invention with acetylene-terminated imides find the same application as known polyimides.

Details for the syntheses of the various compounds of the invention are given below. These examples show the synthesis and polymerization of both homopolymers and copolymers of the invention. The examples detail the tailorability of the thermomechanical properties of the polymers.

EXAMPLES

Example 1. Synthesis of 3-TMS-ethynylbromobenzene (1') (C$_{11}$H$_{13}$BrSi) MW=253

1,3-Dibromobenzene (247 g, 1.05 mol), trimethylsilylacetylene (105 g, 1.07 mol), triethylamine (180 g, 1.78 mol), and toluene (200 mL) were dissolved with stirring in a dry nitrogen purged 1 L flask. Dry nitrogen was bubbled through this solution for 30 minutes. After removal of the bubbler, tetrakistriphenylphosphine palladium (1.0 g, 0.86 millimol) was added. The components of the reaction were heated to 90° C. The reaction was monitored at intervals by capillary gas chromatography. Further addition of the palladium catalyst was made over 90 hours (total catalyst added: 4.6 g, 0.4 mol % based on dibromobenzene). The reaction mixture was cooled, and the contents filtered to remove the triethylamine hydrobromide by-product. The solution was concentrated on a rotary evaporator and then fractionally distilled through a ten inch Vigreux column to give dibromobenzene (b.p. 55° C./0.20 torr, 110 g, 0.47 mol). The fractionating column was replaced with a short path distillation unit. The product, 3-TMS-ethynylbromobenzene (b.p. 75° C./0.20 torr, 95 g., 0.38 mol), was collected. This corresponded to a 66% yield based on recovered dibromobenzene. The compound had the following spectral characteristics:

$^1$H-NMR (CDCl$_3$) 7.61 (m, 1H), 7.45–7.32 (m, 2H), 7.13 (t, 1H), 0.22 (s, 9H);

$^{13}$C-NMR (CDCl$_3$) 134.6, 131.5, 130.4, 129.6, 125.0, 121.9, 103.2, 95.8, −0.2;

$^{29}$Si-NMR (CDCl$_3$) −17.40;

IR (thin film) 3064, 2960, 2163, 1588, 1559, 1471, 1404, 1250, 874, 843, 782, 760, 644 cm$^{-1}$.

Example 2. Synthesis of 3-TMS-ethynylphenyldimethyl silane (2') (C$_{13}$H$_{20}$OSi$_2$) MW=232

The above-described 3-bromo-TMS protected phenyl acetylene (46.5 g, 0.18 mol) from Example 1 was dissolved in dry ethyl ether (300 mL) and cooled to 0° C. A solution of n-butyl lithium (1.6M in hexane, 130 mL, 0.21 mol) was added to the aryl bromide over a period of 30 minutes. The reaction mixture was stirred an additional hour, and then the metalated aryl halide was added to a solution of chlorodimethylsilane (29 g, 0.3 mol) in ether (100 mL) at 0° C. over a period of 1 hour via a double tipped stainless steel needle. The contents of the reaction flask were stirred at room temperature overnight and then filtered to remove the lithium chloride by-product. Concentration of the clear solution on a rotary evaporator, followed by distillation at reduced pressure, gave the product 3-TMS-ethynylphenyldimethyl silane (b.p. 78° C./0.25 torr, 31.4 g, 0.14 mol. 78% yield). The compound had the following spectral characteristics:

$^1$H-NMR (CDCl$_3$) 7.65 (m, 1H), 7.47 (m, 2H), 7.31 (m, 1H), 4.43 (septet, J=3.7 Hz, 1H), 0.34 (d, J=3.7 Hz, 6H), 0.26 (s, 9H);

$^{13}$C-NMR (CDCl$_3$) 137.6, 137.4, 133.9, 132.6, 127.6, 122.8, 105.3, 94.0, 0.0, −3.9;

$^{29}$Si-NMR (CDCl$_3$) −16.67, −17.77.

Example 3. Synthesis of 3-ethynylphenyldimethyl methoxy silane (3') (C$_{11}$H$_{14}$SiO) MW=190

The above-described TMS protected ethynylphenyl silane (5.0 g, 0.021 mol) from Example 2 was dissolved in anhydrous methanol (40 mL). A small amount of anhydrous potassium carbonate (0.1 g) was added. Hydrogen was evolved over a period of 2 hours. After four hours, the contents of the reaction flask were concentrated on a rotary evaporator and then taken up in dry ethyl ether. The solution was filtered, then fractionally distilled to give the product (b.p. 57° C./0.20 torr, 3.8 g, 0.02 mol, 95% yield). The compound had the following spectral characteristics:

$^1$H-NMR (CDCl$_3$) 7.7 (m, 1H), 7.55 (m, 2H), 7.33 (m, 1H), 3.43 (s, 3H), 3.1 (s, 1H), 0.38 (s, 6H);

$^{13}$C-NMR (CDCl$_3$) 137.8, 137.1, 133.6, 133.1, 127.8, 121.7, 83.8, 77.3, 50.6, −2.4;

$^{29}$Si-NMR (CDCl$_3$) 9.24;

IR (thin film) 3293, 2958, 2832, 1466, 1385, 1254, 1114, 1086, 859, 842, 783, 695, 636 cm$^{-1}$.

Example 4. Synthesis of 3-TMS-ethynylphenyldimethyl silanol (4') (C$_{10}$H$_{12}$SiO) MW=176

The above-described methoxysilylphenylacetylene (1 g, 0.0053 mol) from Example 3 was dissolved in a 10% solution of water in tetrahydrofuran (18 mL). Gas chromatographic analysis of the reaction showed the hydrolysis to be complete in 18 hours. Addition of traces of acid or base to this reaction greatly speeds the hydrolysis but also facilitates the condensation. The reaction flask contents were concentrated on a rotary evaporator, taken up in chloroform, and washed twice with distilled water. The organic layer was dried over anhydrous sodium sulfate and carefully concentrated at room temperature to give a colorless mobile liquid (0.89 g, 96% yield). The silanol had the following spectral characteristics:

$^1$H-NMR (CDCl$_3$) 7.69 (m, 1H), 7.49 (m, 2H), 7.27 (m, 1H), 4.77 (brd s, 1H), 3.08 (s, 1H), 0.32 (s, 6H);

$^{13}$C-NMR (CDCl$_3$) 140.0, 136.5, 133.1, 132.6, 127.4, 121.4, 83.7, 77.0, −0.3;

$^{29}$Si-NMR (CDCl$_3$) 4.82.

Example 5. Synthesis of bis(3-ethynylphenyl)tetramethyldisiloxane (Formula A') (C$_{20}$H$_{22}$Si$_2$O) MW=334

The above-described ethynyl silanol (5.0 g, 0.028 mol) from Example 4 was dissolved in dry benzene (40 mL) and a trace of p-toluene sulfonic acid was added. The reaction was refluxed for 4 hours. Gas chromatographic analysis of the reaction mixture showed the condensation to be complete. The solution was washed well with water, dried over sodium sulfate, concentrated, and distilled at reduced pressure to give a pale yellow liquid (b.p. 125° C./0.01 torr, 4.2 g, 88% yield). Differential scanning calorimetric analysis of this liquid showed the characteristic exotherm of acetylene polymerization at 180° to 250° C. The heat of reaction was 70 calories/gram. The liquid had the following spectral characteristics:

$^1$H-NMR (CDCl$_3$) 7.68 (m, 2H), 7.55 (m, 4H), 7.31 (m, 2H), 3.09 (s, 2H), 0.36 (s, 12H);

$^{13}$C-NMR (CDCl$_3$) 139.8, 136.6, 133.1, 132.9, 127.6, 121.6, 83.9, 77.1, 0.6;

$^{29}$Si-NMR (CDCl$_3$) −0.82;

IR (thin film) 3296, 2957, 2928, 1465, 1385, 1257, 1114, 1062, 858, 786 cm$^{-1}$.

Example 6. Equilibration of octamethyl tetracyclosiloxane and 1,3-bis(3-ethynylphenyl)tetramethyldisiloxane Into a round bottomed flask (50 mL) was placed one drop of a methanol solution of tetramethyl ammonium hydroxide (20% base). The methanol was evaporated and then octamethyl tetracyclosiloxane (D4, 2.0 g, 0.0068 mol) and bis(3-ethynylphenyl)tetramethyldisiloxane (0.5 g, 0.0015 mol) from Example 5 were added to the flask. The reaction mixture was stirred magnetically and heated for 12 hours at 100° C. A small aliquot was analyzed by gas chromatography and the reaction judged complete. The flask contained at this point about 10% by weight D4 and 90% by weight mixed oligomers of D4 and the endcapping ethynylphenyldimethyl siloxane. The reaction was cooled, taken up in hexane, and washed three times with saturated ammonium chloride to remove the base. The solution was dried over sodium sulfate and evaporated on a rotary evaporator to give a pale yellow mobile liquid (2.2 g, 88% yield). Differential scanning calorimetric analysis of this liquid (argon, 10° C./minute) showed the characteristic exotherm of acetylene polymerization at 200° to 275° C. The heat of reaction was 15 calories/gram. The molecular weight (number average by $^1$H NMR) was 1800. The liquid had the following spectral characteristics:

$^1$H-NMR (CDCl$_3$) 7.68 (m, 2H), 7.55 (m, 4H), 7.31 (m, 2H), 3.06 (s, 2H), 0.35 (s, 12H), 0.09 (brd s, 101H);

$^{13}$C-NMR (CDCl$_3$) 140.2, 136.7, 133.2, 132.7, 127.5, 121.5, 83.9, 77.0 (s, all 2C), 1.00 (s, 34C), 0.6 (s, 4C);

$^{29}$Si-NMR (CDCl$_3$) −2.63 (s, 2Si), −20.33 (s, 2Si), −21.85 (s, 17Si);

IR (thin film) 3306, 2963, 2905, 1412, 1261, 1092, 1022, 860, 802 cm$^{-1}$.

Example 7. Polymerization of (alpha, omega)phenylacetylene terminated linear dimethylsiloxanes and characteristics of the materials made thereof Each of the D4-equilibrated bis(3-ethynylphenyl)tetramethyldisiloxane from Example 6 and bis(3-ethynylphenyl)tetramethyldisiloxane from Example 5 were polymerized by heating to 250° C. for 4 hours.

Bis(3-ethynylphenyl)tetramethyldisiloxane gave a clear brown glass which was characterized by thermal analysis and Fourier transform infrared Spectroscopy (FTIR). Thermal gravimetric analysis in argon showed no mass loss until 450° C. and then a 74% char yield to 1000° C. No glass transition was obvious. The coefficient of thermal expansion of the material varied between 55 micrometer/meter/°C. at −100° C. to 120 micrometer/meter/°C. at 350° C. FTIR 3043, 2955, 2901, 1705, 1589, 1474, 1396, 1254, 1119, 1034, 829, 783 cm$^{-1}$.

The D4-equilibrated bis(3-ethynylphenyl)dimethyl siloxane with molecular weight 1800 gave after a cure schedule (the cure schedule is given in Example 8, below) a golden soft rubber which was characterized by thermal analysis and FTIR. Thermal gas analysis in argon showed no weight loss to 450° C. and then a 27% char yield to 1000° C. The coefficient of thermal expansion of the glass phase was 33 micrometer/meter/°C. The glass transition temperature of this material was −107° C. The coefficient of thermal expansion of the rubber phase was 372 micrometer/meter/°C. FTIR (neat, diamond cell) 2963, 2905, 1412, 1261, 1092, 1022, 894, 802 cm$^{-1}$.

Other oligomeric m-phenylethynyl siloxanes were made in a like manner using different ratios of D4 and bis(3-ethynylphenyl)dimethyl siloxane. There was obtained from one reaction which was an equilibration of equal amounts of D4 and bis(3-ethynylphenyl)dimethyl siloxane a mixture of oligomeric (alpha, omega)-phenylethynyl terminated siloxanes with number average equivalent weight of 740 and having the following spectral characteristics:

1H-NMR (CDCl₃) 7.68 (m, 2H), 7.55 (m, 4H), 7.31 (m, 2H), 3.06 (s, 2H), 0.35 (s, 12H), 0.09 (brd s, 32H);

13C-NMR (CDCl₃) 140.2 (m, oligomeric C—Si, 2C), 136.7, 133.2, 132.8, 127.6, 121.6, 84.0, 77.1 (s, all 2C), 1.18 (s, 4C), 1.07 (s, 8C), 0.6 (s, 4C);

29Si-NMR (CDCl₃) −2.63 (s, 2Si), −20.34 (s, 2Si), −21.85 (s, 4Si).

The above-described oligomeric (alpha, omega)-phenylethynyl terminated siloxanes with number average equivalent weight of 740 were polymerized by heating to 250° to 350° C. The resulting polymer had a coefficient of thermal expansion of 88 micrometer/meter/°C. in the glass phase, a glass transition temperature of −27° C. and a coefficient of thermal expansion in the rubber phase of 270 micrometer/meter/°C.

In another reaction which was an equilibration of 0.5 g D4 and 1.5 g bis(3-ethynylphenyl)dimethyl siloxane, there was obtained a mixture of oligomeric (alpha, omega)phenylethynyl terminated siloxanes with number average equivalent weight of 540 and having the following spectral characteristics:

1H-NMR (CDCl₃) 7.68 (m, 2H), 7.55 (m, 4H), 7.31 (m, 2H), 3.06 (m, 2H), 0.35 (m, 12H), 0.09 (m, 18H). The degeneracy of the Si-methyl protons were incomplete at this low molecular weight.

13C-NMR (CDCl₃) 140.2 (m, oligomeric C—Si, 2C), 136.7, 133.2, 132.9, 127.6, 121.6, 84.0, 77.1 (s, all 2C), 1.17 (s, 4C), 1.07 (s, 4C), 0.6 (s, about 3C);

29Si-NMR (CDCl₃) peaks at −0.35, −2.12, −18.5, −19.8, and −21.2 in the ratio of about 1:3:1:3:4.

The above-described oligomeric (alpha, omega)-phenylethynyl terminated siloxanes with number average equivalent weight of 540 were polymerized by heating to 250° to 350° C. The resulting polymer had a coefficient of thermal expansion of 114 micrometer/meter/°C. in the glass phase, a glass transition temperature of −60° C., and a coefficient of thermal expansion of 230 micrometer/meter/°C. in the rubber phase.

Example 8. Formation of Copolymers with Acetylene-Terminated Imides

Acetylene-terminated siloxane oligomers of 740 and 1900 molecular weight from Example 6 were each incorporated into a fluorinated polyimide, commercially available from National Starch under the trade designation FA700. With the appropriate solvent, these silicones could be incorporated into the polyimide. The silicones were homogeneously finely dispersed particles in the cured polyimide matrix. These dispersed particles resulted in improved toughness of the cured polyimide.

Two formulations for each molecular weight silicone were prepared:
(a)
5% silicone:
50 mg silicone (740 mw or 1900 mw)
950 mg imide
2.1 g solvent; and
(b)
10% silicone:
100 mg silicone (740 mw or 1900 mw)
900 mg imide
2.1 g solvent.

Methyl isobutyl ketone was found to form clear, homogeneous solutions for both molecular weights of the silicone at both 5% and 10% silicone loadings.

Dimethylacetamide only worked with 5% 740 mw silicone, to form a homogeneous solution. N-methyl pyrrolidone did not work in any formulation.

Another ketone solvent, cyclohexanone, was tried in the 5% and 10% 740 mw silicone loading formulations, and homogeneous solutions were obtained.

The solutions were cast onto clean glass plates with a 10 mil (0.0254 cm) doctor blade. The coated plates were baked and cured in a nitrogen purged oven at the following schedule:
1 hour at 170° C.
2 hours at 230° C.
3 hours at 300° C.
and then slowly cooled to ambient under nitrogen.

The cured films showed very fine particles of the silicone dispersed homogeneously in the polyimide matrix.

Thus, there has been described acetylene-terminated siloxane monomers, oligomers, polymers thereof, and copolymers with imide polymers. It will be readily appreciated by those skilled in this art that various changes and modifications of an obvious nature may be made without departing from the scope of the invention, as defined by the appended claims.

What is claimed is:

1. An acetylene-terminated siloxane monomer having Formula A

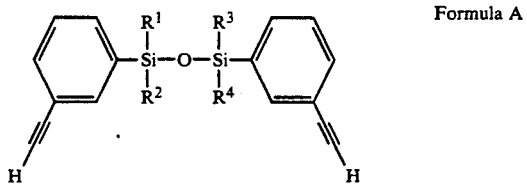

Formula A where $R^1$ and $R^2$ are independently $C_1$ to $C_6$ alkyl, phenyl, or phenyl substituted with one or more $C_1$ to $C_6$ alkyl or halogen groups.

2. The monomer of claim 1 wherein $R^1$ and $R^2$ are each methyl.

3. An acetylene-terminated siloxane oligomer having Formula B

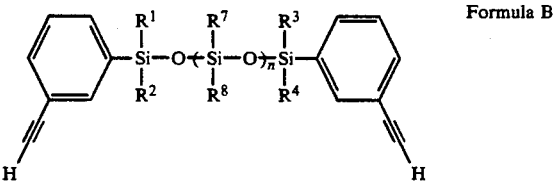

Formula B where $R^1$, $R^2$, $R^3$, and $R^4$ are independently $C_1$ to $C_6$ alkyl, phenyl, or phenyl substituted with one or more $C_1$ to $C_6$ alkyl or halogen groups, $R^7$ and $R^8$ are independently hydrogen, $C_1$ to $C_6$ alkyl, phenyl, or phenyl substituted with one or more $C_1$ to $C_6$ alkyl or halogen groups, and n=1 to 20.

4. The oligomer of claim 3 wherein $R^1$, $R^2$, $R^3$, $R^4$, $R^7$, and $R^8$ are each methyl.

* * * * *